United States Patent [19]
Belter

[11] Patent Number: 5,973,215
[45] Date of Patent: Oct. 26, 1999

[54] PROCESS FOR SEPARATING AND RECOVERING HYDROGEN FLUORIDE FROM MIXTURES

[75] Inventor: Randolph K. Belter, Zachary, La.

[73] Assignee: LaRoche Industries Inc, Atlanta, Ga.

[21] Appl. No.: 09/039,515

[22] Filed: Mar. 16, 1998

[51] Int. Cl.$^6$ .................................................. C07C 17/38
[52] U.S. Cl. .......................................... 570/177; 570/180
[58] Field of Search ..................................... 423/484, 483, 423/488, 462, 240 R; 570/177, 178, 179, 180

[56] References Cited

U.S. PATENT DOCUMENTS 5,632,966  5/1997  Van Der Puy et al. ................. 423/484
5,684,219  11/1997  Boyce et al. ............................. 570/177

*Primary Examiner*—Elli Peselev
*Attorney, Agent, or Firm*—Richard J. Hammond

[57] ABSTRACT

A process is disclosed for the liquid phase separation and recovery of hydrogen fluoride from a mixture comprising hydrogen fluoride and a fluorinated organic hydrocarbon. The process requires that the mixture be treated with a sufficient amount of a coupled phase-separating agent comprising an organic or inorganic salt, an alkanolamine or mixtures thereof and a substituted or unsubstituted aromatic compound to form a first and a second phase. The first phase that is formed is a hydrogen fluoride-rich phase that additionally contains substantially all of said salt, said alkanolamine or mixtures thereof from the coupled phase-separating agent. The second phase comprises substantially all of said aromatic compound and the fluorinated organic hydrocarbon. It is substantially free of hydrogen fluoride. The phases are separated from each other. Hydrogen fluoride and the salt, alkanolamine or mixtures thereof are then recovered from the separated first phase and the aromatic compound and fluorinated organic hydrocarbon are recovered from the separated second phase.

17 Claims, No Drawings

PROCESS FOR SEPARATING AND RECOVERING HYDROGEN FLUORIDE FROM MIXTURES

FIELD OF INVENTION

This invention relates to a process for recovering hydrogen fluoride from a mixture containing hydrogen fluoride and halogenated organic hydrocarbons. This invention is particularly useful in recovering and separating hydrogen fluoride from mixtures that also contain fluorinated organic compounds.

BACKGROUND OF THE INVENTION

The replacement of chlorofluorocarbons (CFC's) widely used in refrigerant compositions, propellants and cooling fluids as well as blowing agents, solvents and rinse agents with environmentally acceptable alternatives has produced an abundance of compounds meeting one or more of these needs. The most acceptable replacement compounds are those having little or no chlorine, since it is generally accepted that chlorinated aliphatics lead to unacceptable reactive chlorine-containing radicals when present in the upper atmosphere. These radicals are thought to react with the ozone in the stratosphere depleting it to dangerously low levels.

One of the more promising alternatives to CFC's are the aliphatic compounds where chlorine has been partially or completely replaced with fluorine. These materials are known respectively as hydrochlorofluorocarbons (HCFC's) and hydrofluorocarbons (HFC's). Typical HCFC's and HFC's have atmospheric lifetimes and global warming potentials that are a fraction of their fully chlorinated analogs. However, many of their other physical properties (low flammability and toxicity, sufficient volatility, etc.) are identical or similar to the CFC's. Accordingly, they are attractive replacements for the chlorinated molecules.

In processes for preparing HCFC's and HFC's, a usual starting material is the chlorinated analog of the desired fluorinated compound. Thus, U.S. Pat. No. 2,787,646 discloses that $SbF_3Cl_2$ and $SbF_3$ are useful for converting compounds of the formula $CMZ_2CX=CHY$, for example 3,3,3-trichloroprop-1-ene or 1,1,3-trichloroprop-1-ene to compounds of the formula $CF_3CX=CHY$, for example 3,3,3-trifluoroprop-1-ene.

The preparation of 1-chloro-1,1,3,3,3-pentafluoropropane and of 1,1,1,3,3,3-hexafluoropropane from 1,1,1,3,3,3-hexachloro-propane in the liquid phase is described in EPO Publication No. 0 522 639 A1. While the preferred catalyst for the reaction is noted to be $SbCl_5$, other catalysts disclosed are those metal chlorides, fluorides, and chloride fluorides of Group IIIa, IVa, IVb, Va, Vb and VIb of The Periodic Table of the Elements.

The processes disclosed above are illustrative of reactions that generate mixtures of hydrogen fluoride and fluorinated organic hydrocarbons. Also present in such mixture are organic by-products, hydrogen chloride, unreacted starting materials and the like. The most commonly practiced separation process for such a mixture is distillation, which facilitates the recovery of hydrogen fluoride for recycle. Unfortunately, the organic fraction that is recovered in these distillation processes also contains residual hydrogen fluoride, especially in cases where hydrogen fluoride/fluorinated organic hydrocarbon constant boiling mixtures occur. Typically, the residual hydrogen fluoride is removed by scrubbing with water and/or alkali. The process is expensive and time consuming generating wastes that require disposal and diminishing the yield of recovered hydrogen fluoride.

Unexamined Japanese Patent Application No. 56226-1996, filed Mar. 13, 1996, incorporated herein by reference, discloses a method for separating hydrogen fluoride from hydrogen fluoride mixtures with 1,1,1,3,3-pentafluoropropane by adding to such mixtures an aromatic compound such as benzene, toluene or trifluoromethylbenzene.

A method of recovering hydrogen fluoride from the above mixtures has been described in our patent U.S. Pat. No. 5,684,219, where an organic or inorganic salt is added to a mixture containing certain fluorinated propanes and hydrogen fluoride.

Other similar methods are disclosed in U.S. Pat. No. 5,632,966 and WO 97/13719.

SUMMARY

The process of the present invention to separate and recover hydrogen fluoride from mixtures of hydrogen fluoride and fluorinated organic hydrocarbons utilizes the addition to such mixture a composition that is an organic or inorganic salt, a lower alkanolamine or mixtures thereof and a substituted or unsubstituted aromatic compound. This composition is sometimes referred to herein as a "coupled phase-separating agent". Such addition causes the mixture to separate into two phases. One phase is hydrogen fluoride-rich and additionally contains most of the organic or inorganic salt, the alkanolamine or mixtures thereof. The other phase is substantially free of hydrogen fluoride and is rich in the fluorinated organic hydrocarbon and additionally contains the substituted or unsubstituted aromatic compound. The phases cleanly separate. As such, the fluorinated organic compound phase can be readily separated from the hydrogen fluoride phase. Each of the two separated phases can be further processed to recover, individually, the fluorinated organic compound and the organic or inorganic salt, lower alkanolamine or mixtures thereof (from the fluorinated organic hydrocarbon-rich phase) and hydrogen fluoride and the substituted or unsubstituted aromatic compound (from the hydrogen fluoride-rich phase).

DESCRIPTION OF THE PREFERRED EMBODIMENTS

The process of the present invention is particularly useful for recovering hydrogen fluoride from liquid mixtures comprising hydrogen fluoride and highly fluorinated organic compounds. It is well known to those skilled in the art, that recovering and separating the majority of hydrogen fluoride contained in such mixtures may be very difficult. Typical recovery processes, for example, a distillation process may prove ineffective because of the formation of constant boiling mixtures, boiling points of the components of the mixtures are too close to each other, etc. The present invention is a relatively simple and effective method to effect such a separation and is accomplished merely by adding to the liquid mixture a composition comprising an organic or inorganic salt, an alkanolamine or mixtures thereof and an aromatic compound that is substituted or unsubstituted, such composition being soluble in said liquid mixture, i.e., it forms a solution which cause the phase separation effect in accordance with the process of the present invention.

The process of the present invention effects the separation of hydrogen fluoride from mixtures comprising hydrogen fluoride and highly fluorinated organic compounds by adding to such mixtures compositions comprising an organic or inorganic salt, a lower alkanolamine or mixtures thereof and a substituted or unsubstituted aromatic compound.

The term "lower alkanolamine" is intended to mean $C_1$ to $C_6$ alkylene groups substituted by at least one amino group and at least one hydroxy group. Thus, they have the general formula $[HO\text{-}(CH_2)_x]_y NH_z$ where x is 1 to 6, y is 1, 2 or 3, z is 0, 1 or 2 and the sum of y and z is 3. Such compounds include, for example, ethanolamine, diethanolamine, triethanolamine and the like.

The term "substituted or unsubstituted aromatic compound" is intended to mean benzene or a phenyl group substituted with at least one substituent selected from the group consisting of halo, for example fluoro, chloro, bromo, etc.; $C_1$ to $C_6$ alkyl, for example methyl, ethyl, n-propyl, i-propyl, n-butyl, etc.; and halo substituted $C_1$ to $C_6$ alkyl, for example fluoromethyl, trifluoromethyl, etc.

Preferred substituted aromatic compounds of use in the coupled phase-separating composition of the present invention are chlorobenzene, 1,4-dichlorobenzene, toluene, xylene, trimethylbenzene, tetramethylbenzene, 1-methyl-2-ethylbenzene, 1,3-dimethyl-4-ethylbenzene, 4-chlorotoluene, trifluoromethylbenzene, 1,3-bistrifluoromethylbenzene, 4-trifluoromethyltoluene and the like.

In the process of the present invention, the term "organic or inorganic salt" is intended to mean the ammonium, $C_1$–$C_4$ alkylammonium and Group Ia cationic salts of organic acids such as carboxylic acids, e.g., di and trifluoroacetic acids; the sulfonic acids, e.g. $C_1$–$C_4$ alkyl-sulfonic acids(methyl sulfonic acid, etc.),unsubstituted and $C_1$–$C_4$ alkyl-substituted aryl sulfonic acids (benzensulfonic acid, toluenesulfonic acid, etc.), halosulfonic acids (fluorosulfonic acids, etc.); etc. and the inorganic acids such as hydrofluoric acid, hydrochloric acid, sulfuric acid, phosphoric acid, nitric acid, etc.

The preferred organic salts of use in the process of the present invention are the salts from Group Ia alkali metal (sodium, potassium, cesium, etc.) or salts of ammonium with hydrofluoric acid. Particularly preferred are the mono, di and trifluoride salts of sodium, potassium and ammonium.

In the process of the present invention, the term "hydrogen fluoride-rich phase" is intended to mean a solution comprising substantially only hydrogen fluoride and the salt, alkanolamine or mixtures thereof component of the coupled phase-separating agent that is added to effect separation in accordance with the process of the present invention. This phase is also referred to as the "first phase".

The fluorinated organic compounds that are separated according to the process of the present invention include hydrofluoroalkanes, hydrochlorofluoroalkanes, chlorofluoroalkanes and hydrofluoroethers. The preferred compounds of use in the present invention have the formula

wherein a is 0 or the integer 1 or 2 and b is 0 or the integer 1, 2 or 3. Most preferably these compounds are exemplified by 1,1,1,3,3-pentafluoropropane, 1,2,2,3,3-pentafluoropropane, 1,1,1,3-tetrafluoropropane, and the like.

The term "second phase rich in the fluorinated organic compound" is intended to mean a solution comprising substantially all of the fluorinated organic hydrocarbon and the substituted or unsubstituted aromatic compound that was a component of the coupled phase-separating agent. There is little or no hydrogen fluoride or organic or inorganic salt, alkanolamine or mixtures thereof in this second phase. It is not readily soluble in the first phase.

The separation of hydrogen fluoride from a mixture comprising hydrogen fluoride and a fluorinated organic hydrocarbon, by the addition of a coupled phase separating agent comprising an organic or inorganic salt, an alkanolamine or mixtures thereof and a substituted or unsubstituted aromatic compound, results in the formation of two phases from a mixture that, before addition of the coupled phase separating agent was a single phase. However, it should be noted that in order to successfully produce the two separate phases in accordance with the present invention it is necessary to control the temperature and pressure of the treated mixture so that both the hydrogen fluoride-rich phase and the fluorinated organic hydrocarbon-rich phase remain as liquids. Thus, temperatures that are too high will cause the phases to dissolve, i.e., they become mutually soluble. Temperatures that are too low may result in the crystallization and precipitation of the complex formed between the organic or inorganic salt or alkanolamine or mixtures of such materials and hydrogen fluoride. Temperatures between about −25° C. and about 150° C. are useful to practice the process of the present invention. Preferred temperatures are between about −10° C. to about 125° C., most preferably about 0° C. to about 50° C.

It is well known that the density of solutions of hydrogen fluoride and various metallic salts increases with increasing concentration of such metallic salts. In consideration of the separation of a specific fluorinated organic compound from a mixture, in order to achieve the purposes of the present invention, i.e., to produce two phases comprising a first, hydrogen fluoride-rich phase and a second phase that is rich in the fluorinated organic compound, the amount of coupled phase-separation agent added to the mixture must be closely controlled. Since other variables will effect the separation, i.e. temperature and pressure, as a guide, the concentration of the salt, alkanolamine or mixtures thereof component of the coupled phase-separation agent will typically be from about 1% to about 45% by weight based on the weight of the mixture. Preferably, the concentration of such coupled phase-separation agent is from about 5% to about 40%, most preferably from about 10% to about 20%.

Thus, the concentration of components in the coupled phase-separation agent is critical in obtaining superior recovery of hydrogen fluoride and the fluorinated organic compound. An effective weight ratio of substituted or unsubstituted aromatic compound to the fluorinated organic hydrocarbon is about 1 to 1. However, the amount of substituted or unsubstituted aromatic compound can be from about 0.1% to about 94.9% in the phase separating composition.

In the preferred embodiment of the present invention, a premixture of hydrogen fluoride and the coupled phase-separation agent is made before any addition to the hydrogen fluoride mixture with fluorinated organic hydrocarbon. However, each of the components of the coupled phase-separation mixture can be added separately to such a mixture.

After addition of the coupled phase-separation agent(or the solution of the coupled phase-separation agent in hydrogen fluoride), to the single phase mixture, two phases result. One of the phases is more dense then the other phase and not easily soluble in such phase. It moves to the bottom in the reactor vessel. This lower phase in a typical separation, contains substantially all of the organic or inorganic salt, the alkanolamine or mixtures thereof component of the coupled phase-separation as well as hydrogen fluoride, i.e., it is a hydrogen fluoride-rich phase. This phase is separated from the upper phase and treated by, for example, distillation to recover hydrogen fluoride overhead and the salt, alkanolamine or mixtures thereof component of the coupled phase-separation agent as a residue.

The phase that is substantially free of hydrogen fluoride and rich in the fluorinated organic compound is usually the upper phase. It additionally contains substantially all of the substituted or unsubstituted aromatic compound. It is separated simultaneously with the other phase and may be treated by distillation to separately recover the fluorinated organic compound and the aromatic compound or it can be partly or wholly fed to the reactor used to produce the original mixture, for recycle.

As stated previously, the process of the present invention is applicable to the separation and recovery of hydrogen fluoride from mixtures containing hydrogen fluoride and fluorinated organic compounds. Preferably, the separation and recovery process of this invention is used for compositions which tend to form constant boiling and azeotropic-like compositions. Most fluorinated organic hydrocarbons such illustrated by hydrofluorocarbons, hydrochlorofluorocarbons and hydrofluoroethers form such compositions with hydrogen fluoride. Accordingly, while this process is general in nature, i.e., it can be used to separate hydrogen fluoride from any organic mixture where hydrogen fluoride is not easily removed by distillation, treating mixtures of hydrogen fluoride and hydrofluoroaliphatic, hydrochlorofluoroaliphatic, chlorofluoroaliphatic and hydrofluoroether compounds is the preferred embodiment of the present process.

The following Examples are for purposes of illustration only and should not be regarded as limiting the invention disclosed herein in any manner.

EXAMPLES

Example 1

The following table discloses examples of the separation of mixtures of hydrogen fluoride (HF) and a fluorinated organic compound that is 1,1,1,3,3-pentafluoride (HFC-245fa) according to the process of the present invention.

For convenience and safety in these experiments, sodium bifluoride(NaHF$_2$) was used in place of sodium fluoride and the first equivalent of HF. In the table, the molar equivalents are shown, i.e., NaHF$_2 \leftrightarrows$ NaF+HF.

Sodium bifluoride was placed in a TEFLON® separatory funnel and chilled to 0° C. To this separatory funnel was slowly added HF also chilled to 0° C. A solution of sodium fluoride in HF was formed.

The compounds, chilled to 0° C. shown in the table below were added to the above solution in the amounts set forth below for each of the examples.

In each of the examples, after the compounds had been added to the separatory funnel, the contents were allowed to warm to room temperature. The funnel was then shaken and allowed to settle for one minute. Two layers formed at this point. The HF-containing layer was drawn off and weighed. It was mixed with ice and the organic content determined gravimetrically. Similarly, the organic layer was drawn off and weighed. It was mixed with ice and titrated with dilute sodium hydroxide.

In the case of Example 1a, a solution of the following components was made:
chlorobenzene 50.0 grams with HFC 245fa 50.0 grams; and sodium bifluoride 14.1 grams with HF 51.3 grams.
Mixtures of the following were also made:
Example 1b, chlorobenzene 43.0 grams with HFC 245fa 43.0 grams; and HF 43.0 grams with diethanolamine 26.0 grams.
Example c3, HFC 245fa 54.0 grams; and hydrogen fluoride 44.4 grams with sodium bifluoride 14.1 grams.

Example c4, chlorobenzene 50.0 grams with HFC 245fa 50.4 grams; and HF 23.5 grams.
Example c5, 1,3-bistrifluoromethylbenzene 277.1 grams with HFC 245fa 289.4 grams; and HF 51.2 grams. See Unexamined Japanese Patent Application No. 56226–1996, page 11.
Example c6, HFC 245fa 42.5 grams; and HF 40.7 grams with diethanolamine 21.0 grams.

It should be noted that Examples c1 thru c7 are for comparison purposes only.

| Organic/HF System | Amount of Organic Recovered (%) | Amount of HF in Organic (%) |
|---|---|---|
| c1 Chlorobenzene/HF | 92.0 | 0.91 |
| c2 Chlorobenzene/Sodium Fluoride + HF | 98.8 | 0.27 |
| 1a Chlorobenzene + HFC 245fa/HF + NaF | 97.6 | 0.66 |
| c3 HFC-245fa/HF + NaF | 96.4 | 1.48 |
| c4 Chlorobenzene + HFC-245fa/HF | 67.9 | 3.56 |
| c5 1,3-Bistrifluoromethylbenzene + HFC-245fa/HF | 94.3 | 2.57 |
| c6 HFC 245fa/HF-Diethanolamine | 85.1 | 0.90 |
| c7 Chlorobenzene/HF + Diethanolamine | 99.0 | 0.20 |
| 1b Chlorobenzene + HFC 245fa/HF + Diethanolamine | 95.8 | 0.12 |

The above results demonstrate that superior phase separations are achieved by using the coupled phase separating composition of the present invention.

I claim:

1. A process for the liquid phase-separation of hydrogen fluoride from a mixture comprising hydrogen fluoride and a fluorinated aliphatic hydrocarbon comprising adding to the mixture an amount of a coupled phase-separating agent comprising an organic or inorganic salt, a lower alkanolamine or mixtures thereof and a substituted or unsubstituted aromatic compound, the amount of said coupled phase-separating agent added being sufficient to form a liquid first phase comprising hydrogen fluoride and substantially all of the organic or inorganic salt, lower alkanolamine or mixtures thereof and a liquid second phase, said liquid second phase comprising substantially all of said substituted aromatic compound and being substantially free of hydrogen fluoride and rich in said fluorinated aliphatic hydrocarbon.

2. The process according to claim 1 wherein said fluorinated aliphatic hydrocarbon is a compound of the formula

wherein a is 0 or the integer 1 or 2 and b is 0 or the integer 1, 2 or 3.

3. The process according to claim 1 wherein said salt is an a $C_1$-$C_4$ alkylammonium or Group Ia cationic salt of an organic acid and said aromatic compound is benzene or phenyl substituted with at least one substituent selected from the group consisting of halo, $C_1$ to $C_6$ alkyl and halo substituted $C_1$ to $C_6$ alkyl.

4. The process according to claim 3 wherein said organic acid is selected from the group consisting of a carboxylic acid and a sulfonic acid and said aromatic compound is chlorobenzene.

5. The process according to claim 4 where organic acid is selected from the group consisting of difluoroacetic acid and trifluoroacetic acid.

6. The process according to claim 4 wherein said organic acid is selected from the group consisting of $C_1$–$C_4$ alkylsulfonic acid, unsubstituted and $C_1$–$C_4$ alkyl-substituted aryl sulfonic acid and halosulfonic acid and said aromatic compound is chlorobenzene.

7. The process according to claim 1 wherein said salt is a $C_1$–$C_4$ alkylammonium or Group Ia cationic salt of an inorganic acid.

8. The process according to claim 7 wherein said inorganic acid is selected from the group consisting of hydrofluoric acid, hydrochloric acid, sulfuric acid, phosphoric acid and nitric acid and said aromatic compound is chlorobenzene.

9. The process according to claim 1 wherein said temperature and pressure of the treated mixture is sufficient to cause the first and second phase to remain as liquids.

10. The process according to claim 1 wherein said coupled phase-separating agent comprises a lower alkanolamine and chlorobenzene.

11. The process according to claim 1 wherein said coupled phase-separating agent comprises a compound of the formula

[HO—(CH$_2$)$_x$]$_y$NH$_z$ where x is 1 to 6, y is 1, 2 or 3, z is 0, 1 or 2 and the sum of y and z is 3 and chlorobenzene.

12. The process according to claim 1 wherein said coupled phase-separating agent comprises sodium fluoride and chlorobenzene.

13. The process according to claim 1 wherein said coupled phase-separating agent comprises ethanolamine and chlorobenzene.

14. The process according to claim 1 wherein said coupled phase-separating agent comprises diethanolamine and chlorobenzene.

15. A process for the liquid phase-separation of hydrogen fluoride from a mixture comprising hydrogen fluoride and 1,1,3,3,3-pentafluoropropane comprising adding to the mixture an amount of a coupled phase-separating agent comprising an organic or inorganic salt, a lower alkanolamine or mixtures thereof and a substituted or unsubstituted aromatic compound, the amount of said coupled phase-separating agent added being sufficient to form a liquid first phase comprising hydrogen fluoride and substantially all of the organic or inorganic salt, lower alkanolamine or mixtures thereof and a liquid second phase, said liquid second phase comprising substantially all of said substituted aromatic compound and being substantially free of hydrogen fluoride and rich in 1,1,3,3,3-pentafluoropropane.

16. The process according to claim 15 wherein said phase separating agent comprises sodium fluoride and chlorobenzene.

17. The process according to claim 15 wherein said phase separating agent comprises diethanolamine and chlorobenzene.

* * * * *